United States Patent
Suverkrup et al.

(10) Patent No.: US 6,228,381 B1
(45) Date of Patent: *May 8, 2001

(54) FORM OF ADMINISTRATION FOR APPLYING PHARMACEUTICAL SUBSTANCES AND AUXILIARY SUBSTANCES, AND PROCESS FOR THE PREPARATION THEREOF

(76) Inventors: Richard Suverkrup, Domhofstrasse 24, D-53332, Bornheim; Sabine Grunthal, Am Stammheimer Hauschen 6, D-51061; Michael Diestelhorst, Brauweiler Weg 205, D-50933, both of Koln, all of (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,185
(22) PCT Filed: Mar. 8, 1997
(86) PCT No.: PCT/EP96/00969
    § 371 Date: Apr. 14, 1998
    § 102(e) Date: Apr. 14, 1998
(87) PCT Pub. No.: WO96/27350
    PCT Pub. Date: Sep. 12, 1996

(30) Foreign Application Priority Data

Mar. 7, 1995 (DE) ............................................... 195 08 029

(51) Int. Cl.$^7$ ............................ A61K 31/74; A01N 25/34
(52) U.S. Cl. .................. 424/402; 424/78.02; 424/78.04; 424/443; 424/445; 424/447; 424/449
(58) Field of Search .................................. 424/402, 443, 424/445, 447, 449, 78.02, 78.04

(56) References Cited

FOREIGN PATENT DOCUMENTS

0064841 * 4/1982 (EP).
 19480 * 12/1991 (WO).

* cited by examiner

*Primary Examiner*—Jose' G. Dees
*Assistant Examiner*—Kathryne E. Shelborne
(74) *Attorney, Agent, or Firm*—Antonelli, Terry, Stout & Kraus, LLP

(57) ABSTRACT

A form of administration for applying pharmaceutical substances, auxiliary substances and diagnostic agents including a flexible carrier which is water repellant or is rendered water repellant, having a preparation in the form of a lyophilizate adhering to the carrier. The preparation contains a medicament and a hydrophilic polymer which can swell or is water-soluble. During application, the preparation is detached from the carrier for the purpose of application by rehydration of the preparation on contact with liquid.

21 Claims, 1 Drawing Sheet

FORM OF ADMINISTRATION FOR APPLYING PHARMACEUTICAL SUBSTANCES AND AUXILIARY SUBSTANCES, AND PROCESS FOR THE PREPARATION THEREOF

The invention relates to a presentation form for the application of pharmaceutical active compounds, pharmaceutical auxiliaries, pharmaceuticals and/or diagnostics, comprising a carrier and a preparation attached to the carrier, which is detachable from the carrier on contact with a liquid during the application and a [lacuna] for the production thereof.

EP 0064 841 A1 discloses a presentation form for bringing pharmaceutical agents into contact with body moisture, in which the pharmaceutical agent is contained in a soluble matrix, comprising, for example, a water-soluble polymer, and is applied to a strip as a film and dried.

The dried film comprising the pharmaceutical agent is relatively rigid and does not always dissolve sufficiently rapidly on contact with body moisture. When used in the eye, the dried hard film can also lead to injuries.

The embedding of pharmaceuticals in polymers of hydrophilic monomers in the form of polymer solutions and emulsions as a presentation form has been known for a long time, reference being made, by way of example, to German Patent Specification 26 36 559, Swiss Patent Specification 625 704 or, for use in the eye, German Offenlegungsschrift 24 48 737.

By way of example, reference is made to EP 0507 224 A2, in which eye drops are prepared from an ophthalmic substance and a swellable polysaccharide and instilled into the eye, and swell after instillation.

EP 224 987 A discloses eye drops which contain a polymeric component in the form of soluble or insoluble hyaluronan or hylan and a medicament. The eye drops are present in an aqueous to viscoelastic solution and are instilled into the eye.

DE 24 41 191 A1 discloses a presentation form in which a dried active compound-containing individual dose is applied to a carrier, the carrier employed being plastic or glass, which do not absorb liquids.

WO 91/19480 discloses an active compound dose in the presentation form of a compressed, pressed and lyophilized shaped part, such as a tablet. Compression does improve the strength of the presentation form, but rapid rehydration is prevented by the high density. In addition, there is the danger of further contamination of the product by microorganisms during preparation due to the additional pressing of the active compound.

The manner of application of pharmaceuticals such as ophthalmological preparations in drop form and drop solutions of this type have a number of disadvantages, such as, in particular, inaccurate application due to the person applying them and the tolerability of the active compounds, pharmaceutical auxiliaries, pharmaceuticals and/or diagnostics according to the generic term is proposed, wherein the carrier is hydrophobic or hydrophobized and the preparation contains the pharmaceutical active compound, pharmaceutical auxiliary, pharmaceutical and/or diagnostic and a swellable hydrophilic or water-soluble hydrophilic polymer and is formed as a lyophilizate, the preparation being detachable from the carrier for the purpose of application by means of hydration of the preparation. Advantageous embodiments of the invention can be inferred from the characterizing features of subclaims 2 to 16. To prepare the presentation form according to the invention, a process as claimed in claim 17 is proposed.

The application system developed according to the invention is preservative-free. As a presentation form, it is advantageously suitable for topical application. The hydrophilized preparation contains the pharmaceutical, auxiliary or the diagnostic embedded in a swellable or water-soluble polymer structure, which after wetting with liquid, in particular body fluid, such as mucus, blood, lacrimal fluid or a suitable medium, forms a gel which is automatically detached from the carrier and enters into active combination with the body as a viscous substance solution or substance suspension. For application, the carrier is held at the gripping end and the flexible end, to which the active compound is applied, is brought into contact with the desired body part. It is possible to apply the carrier containing the lyophilized preparation—virtually in the form of "dry drops"—in various ways, for example:

application of medication intra-, pre- and post-operatively local application to mucous membranes therapy of bacterial and viral infections and mycoses predetermined individual dose.

Compared with conventional methods of application of active compounds and auxiliaries and diagnostics, the presentation form according to the invention has the following advantages:

The dosage, for example, of ophthalmological preparations is more precise, because in each case only the amount of active compound for one application is accommodated on a carrier, and the deposition of the hydrated dispersion in the conjunctival sac can be controlled better by the user than instillation and counting of the drops from eye drop bottles.

Preservatives are not necessary, because the carriers are individually sterile-packed, and the packing is only opened immediately before use. Thus possible disadvantageous effects of preservatives, for example damage to the cornea, conjunctiva and Tenon's capsule, which is unavoidable in the case of addition of preservative to ophthalmological preparations, do not apply.

Because the lyophilizate is anhydrous during storage, the stability, especially of active compounds sensitive to hydrolysis, improves.

At the same time, the necessity of adjusting the pharmaceutical solutions to a pH optimal for stability, which as a rule is not physiologically optimal, does not apply. Thus the tolerability of the application of pharmaceuticals and other substances by means of the presentation form according to the invention is further improved.

The duration of release can be prolonged so that the frequency of use can be decreased under certain circumstances compared with conventional drops.

Due to the softness and flexibility of the carrier, the danger of injuries on contact of the presentation form with body parts, such as mucous membranes or the conjunctiva or cornea, which can occur as a result of applicatiors [sic] of conventional methods, such as, for example, pipette tips which consist of relatively solid material, is decreased. This is especially of importance in the case of older patients with an impaired fine motor system, who use the medication themselves.

According to the invention, by choice of the hydrophilic polymer it is possible to control the release of active compound within certain limits.

The invention is seen as the combination of three elements, namely the application of a drop of the solution of a hydrophilic polymer, which can contain pharmacologically active substances, to a hydrophobic carrier, and the preparation of an anhydrous lyophilizate in situ.

Only when these three subaspects are fulfilled at the same time are the aims and advantages according to the invention realized.

The following properties are uppermost here:

1. Rapid rehydration on contact with a liquid, in particular body fluid, such as lacrimal fluid, which is achieved by the hydrophilic polymer in which one or more pharmacologically active substances can be dissolved being present in the form of a highly porous lyophilizate.

2. The detachment of the carrier during rehydration and adhesion to a body part, for example to the conjunctiva, which is achieved by the combination of the hydrophilic polymer with the hydrophobic carrier.

3. The absence of preservatives and the stability of pharmaceuticals sensitive to hydrolysis, whose mutual requirement is freedom from water.

4. The decrease in the danger of injury on contact with this soft flexible carrier.

5. The precise dosage [lacuna] the possibility of dose reduction in comparison with the application of liquid drops from individual and multi-dose containers.

According to the invention, the presentation form for the topical application of pharmaceutical and other substances is designed such that a solid, compact, but flexible optionally soft carrier is available for the preparation, and the substance is applied to the surface of the flexible hydrophobic or hydrophobically finished carrier in anhydrous form dissolved or dispersed in suitable auxiliaries, preferably hydrophilic polymers, as a lyophilizate, coprecipitate or solid solution (also subsequently called a dispersion). The hydrophobic or hydrophobically finished carrier can be a film, in particular a plastic film, a web or a textile material, i.e. a fabric, and has, for example, a strip-like shape.

In the presentation form according to the invention, the lyophilizate, namely the preparation applied to the carrier, is hydrated on contact with water. The hydration can take place during application due to contact with a body fluid. The preparation, i.e. the lyophilizate, however, can also be wetted before use, for example by immersing the tip of the carrier in water or an aqueous solution, in order then to apply the preparation together with the liquid by means of the carrier. The solvent or water, however, can also be released from a depot which is applied to the carrier or embedded therein, see, for example, the embodiment as claimed in the characterizing features of claim 16.

The detachment of the completely or initially only superficially hydrated active compound dispersion of carrier and its adhesion to the body is achieved by expedient adjustment of the following influencing variables:

wetting behavior of the dry dispersion, penetration of aqueous solutions into the dispersion, their swelling and dissolution behavior adequate adhesion of the hydrated dispersion to the body part, such as conjunctiva, with low adhesion to the carrier viscosity and surface tension of the hydrated dispersion.

The proposed carrier is a textile fabric made of natural fibers and/or synthetic fibers and/or filaments or a plastic film. However, it is also possible to prepare the carrier from a combination of two or more layers of fibers and film. The carrier should be so flexible and soft that, on contact with the body part, it cannot injure the latter. The carrier can be produced or coated on the basis of a hydrophobic thermoplastic as claimed in claim 4 if these are physiologically indifferent. Possible webs are, in particular, also meltblown webs made of microfibers, for example on the basis [lacuna] polypropylene, which can be prepared in very low area weights and soft design with hydrophobic properties. Preferably, the carrier for the presentation form is formed as a small strip, having a very soft tongue-like area to which the preparation comprising the active compound, such as pharmaceutical, and the swellable or water-soluble hydrophilic polymer are applied and a further area formed to be somewhat stiffer, in particular by means of reinforcing layers, which is used for manipulating, i.e. for gripping and handling. The presentation form can have a carrier in a width of approximately 4 to 8 mm with a length of approximately 30 to 50 mm.

It is important that the carrier to which the preparation is applied, namely as a lyophilizate, has a hydrophobic surface. This is especially important if, for the purpose of application, the preparation comes into contact with liquid, the preparation swelling [lacuna] that the swelling or dissolving preparation, as a result of the hydrophobicity of the carrier, detaches itself easily from the latter, i.e. virtually detaches itself automatically and adheres mucoadhesively to the eye or other body parts, tissues or the like as a viscous pharmaceutical solution or suspension and acts there.

A number of carrier materials, such as, for example, fluorine-containing polymers, have sufficiently high hydrophobicity such that they are particularly readily suitable as a carrier material for the presentation form according to the invention. On the other hand, it is also possible correspondingly to hydrophobically equip textile fabric made of natural and/or synthetic fibers by means of hydrophobizing techniques and hydrophobizing agents known from the textile industry.

The pharmaceutical application according to the invention formed as a xerogel preparation is lyophilized, i.e. freeze-dried. In this process, the respective active compound, auxiliary or the like is dissolved or dispersed in anhydrous form in physiologically tolerable hydrophilic polymers. The preparation is applied to the carrier, preferably in compact form as small heaps or in drop form. The mass of the xerogel applied, i.e. the preparation comprising the active compound, auxiliary or the like and hydrophilic polymer, can be adapted to any medication, from a small quantity up to gram amount. In the case of ophthalmological preparations, for example, it can be between 0.05 and 0.2 mg, which can be hydrated by about 2 to 6 microliters of liquid, for example lacrimal fluid. The problem of isotonization did not turn out to be so marked here as in the application of larger volumes of aqueous solutions, as is customary with liquid eye drops, since the osmotic pressure of the hydrated surface of the polymer gel of the preparation according to the invention is lower and the release of the pharmaceutical only takes place slowly, because the resulting gel layer acts as a diffusion barrier.

The proportion by weight of pharmaceutical in the preparation is highly dependent on the respective pharmaceutical.

In principle all ophthalmological preparations which are used topically can be used in the eye for the presentation form according to the invention. In particular, it is possible to apply them in the manner according to the invention as a lyophilized preparation in combination with a hydrophilic swellable or water-soluble polymer.

Suitable ophthalmic pharmaceuticals which can be employed in the presentation form according to the invention are, for example, the following pharmaceutical classes: antiallergics, antibiotics, chemotherapeutics, corticosteroids, antiglaucomatological preparations, local anesthetics, mydriatics, nonsteroidal antiinflammatories, alpha-sympathomimetics, virustatics.

The following applies in principle to all pharmaceuticals employable: the lower the pharmaceutical content of an individual dose, the better the pharmaceutical can be incorporated into the presentation form according to the invention as a lyophilizate. The active compound content of the lyophilizate preparation can be in an order of magnitude of up to 20 to 30% by weight of the hydrophilic polymer containing [sic] in the lyophilized preparation.

The invention concerns a presentation form for known pharmaceutical active compounds, auxiliaries and diagnostics which are commercially available and subject to approval.

Hydrophilic polymers and biopolymers, which are either swellable or water-soluble, employed are in particular those substances which are known as physiologically tolerable nontoxic thickeners, in particular hydrocolloids, which form gels or viscous solutions in aqueous systems.

Those suitable for this purpose are, for example, organic natural thickeners from the polysaccharides and biopolymers group, such as agar-agar, carrageenan, tragacanth, gum arabic, alginates, pectins, polyoses, guar gum, carob bean flour, starch, dextrins, gelatin, casein, xanthan and alginic acid (see claim 16). However, modified organic natural substances which are known as thickeners, such as carboxymethylcellulose, cellulose ethers, hydroxyethyl- and -propylcellulose, carob bean flour ethers, can also be employed. However, organic fully synthetic substances are also suitable to be employed as thickeners in the present invention, such as polyvinyl alcohol, polyvinylpyrrolidone, poly(meth)-acrylic acids, poly(meth)acrylates, in order to construct a polymeric swellable or water-soluble structure in which the pharmaceutical is embedded. Polyacrylic acids and polyvinylpyrrolidones are water-soluble, while most of the other thickeners mentioned are mainly swellable and form gels. It is essential that the pharmaceutical is embedded in a swellable or water-soluble polymer structure of hydrophilic polymers, and the polymer structure is able to form a gel or dispersion detaching itself from the carrier on contact with a liquid, for example lacrimal fluid. This detachment is promoted by the hydrophobic finishing of the carrier material.

Preferably, the presentation form according to the invention is formed such that in each case a carrier contains the active compound, auxiliary, diagnostic and pharmaceutical in an amount sufficient for one application. The carrier can be formed of small manipulable strips on which the preparation is mounted in dot form as a small heap and in contact with the body part, such as the eye, contact of the body fluid, such as the lacrimal fluid, absorbs the water and forms a gel or forms a dispersion which detaches itself from the carrier and adheres to the body or eye. Each carrier with preparation is sterile-packed such that problem-free handling and storage of the presentation form according to the invention is facilitated.

A process for preparing a presentation form according to the invention is distinguished in that a) a solution of a swellable or water-soluble, hydrophilic polymer is prepared, b) and the pharmaceutical active compound, pharmaceutical auxiliary, pharmaceutical and/or the diagnostic is incorporated into this solution and dissolved or dispersed therein, whereby a dissolved preparation is obtained, c) the dissolved preparation is applied to a carrier material in a desired dose, in particular added dropwise as drops [sic], d) then the carrier material with the dissolved applied preparation is frozen and subsequently freeze-dried, whereby the dissolved preparation is obtained on the carrier material as a lyophilizate, e) and the presentation forms with loyphilized [sic] preparation are formulated from the carrier material containing the lyophilizates.

During the entire preparation process aseptic conditions are ensured and the measures known per se necessary for the preparation of sterile products are carried out. This applies both to the carrier and the preparation.

A particularly advantageous process for preparing the lyophilizate preparation, comprising a hydrophilic swellable or water-soluble polymer and the medicament or the like, is freeze-drying or lyophilization. The methods of lyophilization are known and commercially available equipment is also obtainable for this purpose. The characteristic feature of freeze-drying is that the removal of the solvent is carried out by sublimation from a frozen preparation. The phase transition liquid to gaseous otherwise taking place during drying is replaced by the phase transitions liquid to solid (freezing) and solid to gaseous (sublimation or freeze-drying in the narrower sense). Beside numerous other special physico-chemical features, this has the result that in a freeze-dried preparation—lyophilizate—polymers or thermo-labile pharmaceuticals (e.g. proteins) are not destroyed, that it is not shriveled, that it has a very large internal surface area, that it is able in a matter of seconds, for example, to dissolve in water again or to be saturated with water. In summary: the original properties of a preparation are optimally retained after freeze-drying. Freeze-dried anhydrous preparations can be stored for a very long time with suitable packing.

It is also possible to develop the presentation form according to the invention further in such a way that it is prepared without pharmaceutical addition and only contains swellable or water-soluble hydrophilic polymer as a lyophilizate. A presentation form formed in such a way in combination with a liquid depot on the carrier as claimed in claim 16 can be used according to the invention as an applicator for artificial lacrimal fluid.

The invention is illustrated in the drawing by two exemplary embodiments.

Figure 1:
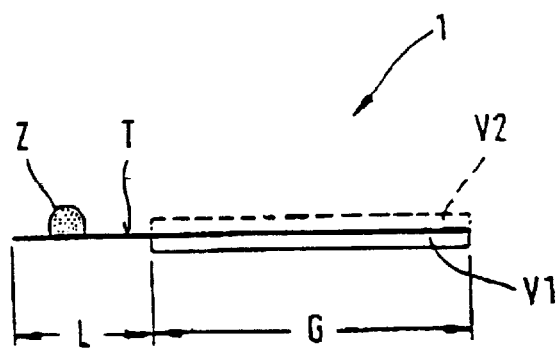
FIG. 1 shows a presentation form in side view.
Figure 2:
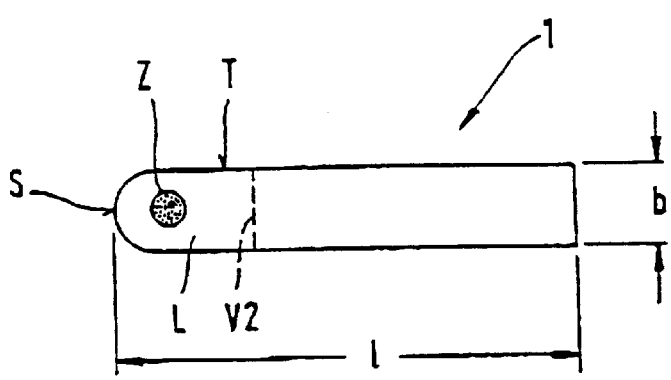
FIG. 2 shows the presentation form in plan view with a preparation

The presentation form 1 according to FIG. 1 comprises the carrier T in strip form made of a flexible thermoplastic, for example a polytetrafluoroethylene film of a thickness of 100 $\mu$m, which is very soft and flexible. In order to impart a higher stability and good grip to the carrier T in the gripping area G, it is intended to reinforce the gripping area with a further layer, for example a textile fabric or film, so that the flexibility and movability of the presentation form is indeed retained in its entirety, but the nonreinforced area is designed to be soft and pliable as a tongue L, so that on contact with the eye and the cornea it causes no injuries. The tongue is rounded off in its front area S. As a whole, the carrier is designed as a strip, having a width b of, for example, 0.5 cm with a length of 3 cm. The gripping area G should in this case be at least 2 cm long, so that good handling is possible. The reinforcing layers V1, V2 can be present both on the bottom and on the top of the carrier. The front nonreinforced part of the carrier C is then more flexible compared with the reinforced area of the carrier. The preparation Z is applied in adhesive or adherent form to the soft, non-reinforced, flexible, tongue-shaped part of the carrier T as a lyophilizate, comprising, for example, the pharmaceutical and the hydrophilic polymer in compact form, for example as a heap or in drop form. The presentation form shown in FIGS. 1 and 2, namely a medicament strip, can now be held in the gripping area and the preparation Z applied in a simple manner to the body part, for example the eye area, by contact. By means of the lacrimal fluid of the eye, the lyophilized preparation Z is swollen or dissolved and detaches automatically from the carrier and adheres to the conjunctiva, where this viscous pharmaceutical solution or suspension acts mucoadhesively.

Figure 3:
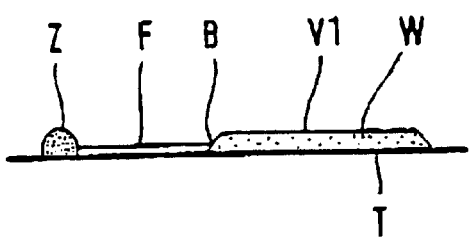
FIGS. 3, 4 show a presentation form in side view and plan view with preparation and liquid depot.
Figure 4:
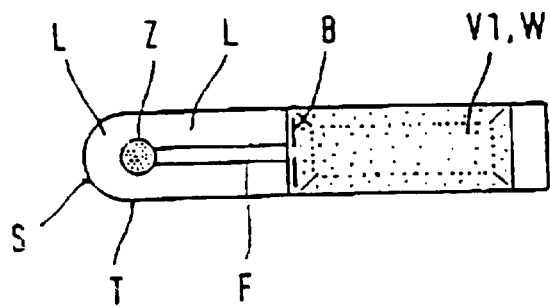

In order to make sure in every case that on application of the lyophilized preparation using the strip presentation form sufficient liquid for the hydration of the preparation is present, it is also possible, as shown in the embodiment according to FIGS. 3 and 4, to provide the carrier, i.e. the presentation form, with a liquid reservoir or depot, for example water for injection or isotonic saline solution. In this case a reinforcing film is fixed to the carrier T with formation of a hollow space and the hollow space is filled with liquid. On one side facing the tongue-shaped part of the carrier with the preparation Z, the reinforcement V1, which covers the liquid, can be provided with an intended breakage site, for example a small slip of paper B which can be torn off, so that on application this slip of paper B is removed and the liquid then flows out of the depot. In order to bring this liquid immediately into contact with the lyophilized preparation Z on the carrier T, a filter strip F, for example, which extends from the preparation Z to the liquid depot W is applied to the carrier. On emergence of the liquid from the opened intended breakage site B, this is absorbed by the filter and inevitably supplied to the preparation Z, so that here in turn the preparation swell [sic] up or goes into solution and a pharmaceutical solution or suspension results which detaches from the hydrophobic carrier and comes into contact with the conjunctiva.

Possible carrier materials are all those compact, woven, knitted or nonwoven fabrics which are physiologically acceptable, which release no fibers or particles and which are so soft that on contact with the body part, such as the cornea or conjunctiva of the eye, that they cause no injuries.

The invention was only shown by way of example in the use of ophthalmological preparations for the eye. The presentation form according to the invention, however, can be used in various ways, for example orally using lyophilizates comprising pharmaceutical active compounds, auxiliaries or diagnostics or in operations on wound surfaces.

The presentation form according to the invention is not restricted to the exemplary embodiments shown and described.

What is claimed is:

1. A presentation form for the application of at least one of pharmaceutical active compounds, pharmaceutical auxiliaries, medicaments and diagnostic agents, comprising a carrier and a preparation attached to the carrier, wherein the preparation is detachable from the carrier on contact with a liquid during application, wherein the carrier is hydrophobic or hydrophobized, and the preparation contains at least one of the pharmaceutical active compound, pharmaceutical auxiliary, medicament and diagnostic agent and a swellable hydrophilic polymer or a water-soluble hydrophilic polymer, and wherein the preparation is in the form of a highly porous lyophilizate, adhering to the carrier the preparation being detachable from the carrier for the purpose of application by rehydration of the preparation on contact with a liquid during application, whereby sufficient adhesion of the rehydrated lyophilizate preparation to a body part is achieved by low adhesion of the rehydrated lyophilizate preparation with the combination of the hydrophilic polymer with the hydrophobic carrier.

2. A presentation form as claimed in claim 1, wherein the carrier is flexible.

3. A presentation form as claimed in claim 1, wherein the carrier is formed from a textile fabric made of at least one of natural fibers, synthetic fibers, filaments and a plastic film.

4. A presentation form as claimed in claim 1, wherein the carrier is produced on the basis of a hydrophobic thermoplastic or the carrier is provided with a coating of a hydrophobic plastic.

5. A presentation form as claimed in claim 1, wherein the preparation is applied to the carrier in a concentrated mass in compact form on one part of the carrier.

6. A presentation form as claimed in claim 1, wherein the carrier is formed as a strip and at least one end of the strip is designed to be a rounded off area and the preparation is applied to the carrier within at least one of the rounded off area and an area adjacent to the rounded off area.

7. A presentation form as claimed in claim 1, wherein the carrier is designed to be at least partially reinforced on at least one side in an area lying outside an area containing the preparation, wherein said carrier is at least partially reinforced with fabrics made of at least one of paper, textile materials and thermoplastic connected adhesively to the carrier.

8. A presentation form as claimed in claim 1, wherein the pharmaceutical active compound, the pharmaceutical auxiliary, pharmaceutical and/or diagnostic is present on the carrier as a hydrophilized preparation in anhydrous form dissolved in a hydrophilic polymer or dispersed in a hydrophilic polymer.

9. A presentation form as claimed in claim 1, wherein the hydrophilic polymers employed for the preparation are thickeners which form gels or viscous solutions in aqueous systems.

10. A presentation form as claimed in claim 1, wherein the hydrophilic polymers employed are organic natural thickeners are selected from the group consisting of polysaccharides and biopolymers.

11. A presentation form as claimed in claim 1, wherein the hydrophilic polymers employed are thickeners made of modified organic natural substances, selected from the group consisting of carboxymethylcellulose, cellulose ethers, hydroxyethylcellulose, hydroxypropylcellulose, and carob bean flour ethers.

12. A presentation form as claimed in claim 1, wherein the hydrophilic polymeric thickeners made of organic fully synthetic substances are employed in the preparation.

13. A presentation form as claimed in claim 1, wherein the pharmaceutical is embedded in a swellable or water-soluble polymer structure of hydrophilic polymers and the polymer structure is able to form a gel which detaches from the carrier on contact with a liquid.

14. A presentation form as claimed in claim 1, wherein the carrier with hydrophilized preparation is stable on storage and preservative-free and anhydrous.

15. A preparation form as claimed in claim 1, wherein the at least one of the pharmaceutical active compound, pharmaceutical auxiliary, pharmaceutical and diagnostic are applied to a carrier in an amount sufficient for one application.

16. A presentation form as claimed in claim 1, wherein a liquid depot, covered with a reinforcing layer, which can be brought into active combination with the preparation via an absorbent connecting material applied to the carrier displaying a wick action is applied to the carrier.

17. A process for producing a presentation form as claimed in claim 1, which comprises
 a) preparing a solution of a swellable or water-soluble, hydrophilic polymer,
 b) incorporating at least one of a pharmaceutical active compound, a pharmaceutical auxiliary, a pharmaceutical and a diagnostic agent into the solution and dissolving or dispersing it therein, whereby a dissolved preparation is obtained, c) applying the dissolved preparation to a hydrophobic or hydrophobized carrier material in a desired dose, d) then freezing the carrier material with the dissolved applied preparation and subsequently freeze-drying it, whereby the dissolved preparation is obtained and adheres to the carrier material as a lyophilizate, e) and manufacturing the presentation form with lyophilized preparation from the carrier material comprising the lyophilizate.

18. A presentation form as claimed in claim 4, wherein the hydrophobic thermoplastic is selected from the group consisting of polyolefins, ethylene copolymers, fluorine-containing polymers selected from the group consisting of polytetrafluoroethylene, polyfluoroethylene-propylene, ethylenetetrafluoroethylene copolymer, polyvinylidene fluoride, perfluoroalkoxy, ethylenechlorotrifluoroethylene copolymer, polychlorotrifluoroethylene, polyvinyl fluoride, polytetrafluoroethylene copolymer with a fluorinated cyclic ether or tetrafluoroethylene-hexa-fluoropropylene-vinylidene fluoride copolymer.

19. A presentation form as claimed in claim 9, wherein the hydrophilic polymers employed for the preparation are thickeners which are hydrocolloids.

20. A presentation form as claimed in claim 10, wherein the polysaccharides and biopolymers are selected from the group consisting of as agar-agar, carrageenan, tragacanth, gum arabic, alginates, pectins, polyoses, guar gum, carob bean flour, starch, dextrins, gelatin, casein, xanthan and alginic acid.

21. A presentation form as claimed in claim 12, wherein hydrophilic polymeric thickeners made of organic fully synthetic substances are selected from the group consisting of polyvinyl alcohol, polyvinylpyrrolidone, poly(meth) acrylic acids and poly(meth)acrylates.

* * * * *